United States Patent [19]
Brenman et al.

[11] Patent Number: 5,865,774
[45] Date of Patent: Feb. 2, 1999

[54] LUMBO-SACRAL SUPPORT

[76] Inventors: Leonid Brenman, 314 Roebling St., Brooklyn, N.Y. 11211; Jack D'Angelo, 3 Carpeonder Rd., New Brunswick, N.J. 08901

[21] Appl. No.: 953,365

[22] Filed: Oct. 17, 1997

[51] Int. Cl.$^6$ ........................................... A61F 5/00
[52] U.S. Cl. ........................ 602/19; 128/112.1; 601/134
[58] Field of Search ................. 602/19; 601/134; 128/106.1, 108.1, 112.1, 115.1

*Primary Examiner*—Linda C. Dvorak
*Attorney, Agent, or Firm*—Ilya Zborovsky

[57] ABSTRACT

A lumbo-sacral support has a support, comprising a supporting element placeable on a user's body and having an outer surface and an inner surface adapted to face a user's body, the supporting element having opposite ends connectable with one another and being provided on the inner surface with a plurality of projections to apply pressure to the user's body.

6 Claims, 1 Drawing Sheet

LUMBO-SACRAL SUPPORT

BACKGROUND OF THE INVENTION

The present invention relates generally to lumbo-sacral supports.

It is known that lumbo-sacral supports are used to support the back area in the event of various back problems and other related ailments. The known lumbo-sacral supports are formed as belts which are tightly applied to the user's back. It is believed that they can be further improved in the sense of providing an active action on the corresponding area of the user's body.

SUMMARY OF THE INVENTION

Accordingly, it is an object of the present invention to provide lumbo-sacral support which is a further improvement of existing supports.

In keeping with these objects and with others which will become apparent hereinafter, one feature of present invention resides, briefly stated, in a lumbo-sacral support which has a supporting element applicable on a user's body in the area of a user's back and having an outer surface and an inner surface, and a plurality of projections provided on the inner surface so as to apply an active pressure in a plurality of local points to the user's body in this area.

When the lumbo-sacral support is designed in accordance with the present invention, it is substantially more efficient in alleviation of corresponding back and other problems.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
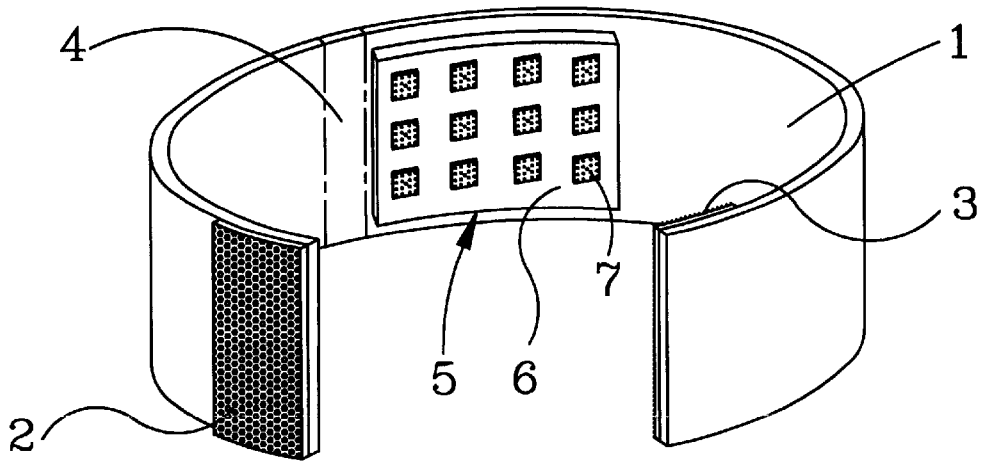
FIG. 1 of the drawings is a perspective view showing a lumbo-sacral support in accordance with the present invention.
Figure 2:
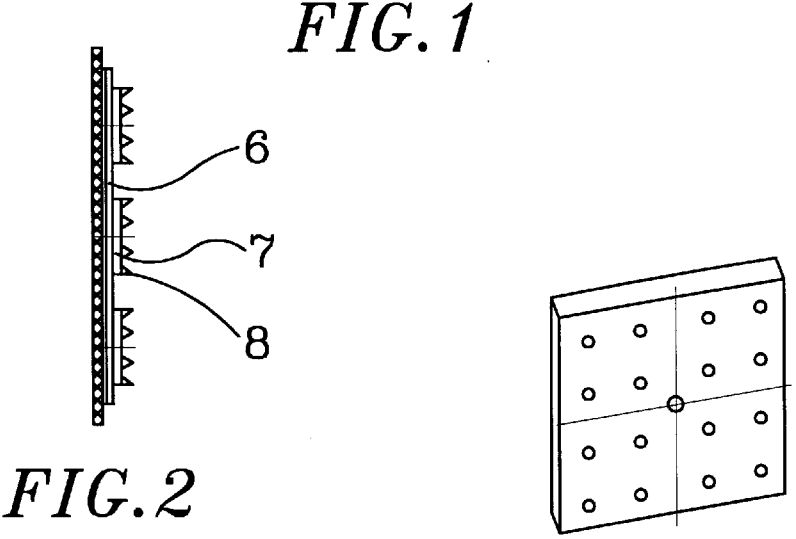
FIG. 2 is a view showing an attachment to a supporting element of the inventive lumbo-sacral support in a transverse cross-section.
Figure 3:
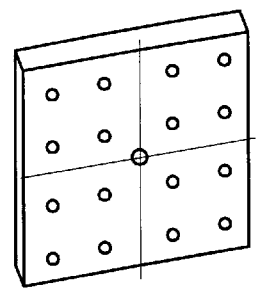
FIG. 3 is a front view of an individual pressure applying element of the inventive lumbo-sacral support.
Figure 5:
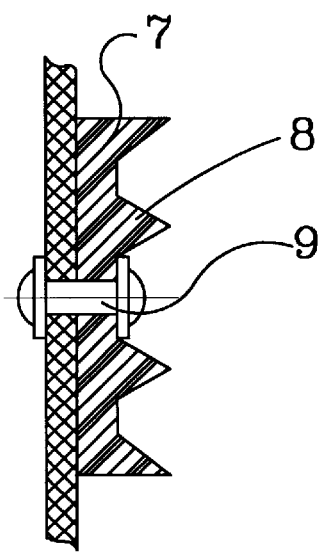
FIG. 5 is a view showing a cross-section of the inventive support.
Figure 4:
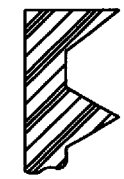
FIG. 4 is a view showing a fragment of a cross-section of the pressure applying element.

A lumbo-sacral support in accordance with the present invention has a supporting element which is identified as a whole with reference numeral 1. The supporting element 1 is formed as a belt which has two ends. In order to hold the supporting element 1 on a user's body in the region of his back, the opposite ends of the supporting element 1 are provided with connecting means. The connecting means can be formed by two pieces 2 and 3 which are arranged on opposite ends of the supporting element 1, with one connecting piece 2 which is fixed on the outer surface of the one end and the other connecting piece which is fixed on the inner surface of another end. The pieces 2 and 3 are provided with a plurality of interengaging formations, for example hooks and loops, as well known in the art. The supporting element 1 can have at least one elastic portion 4 which allows stretching of the supporting element to adjust it to various sizes of the users.

The lumbo-sacral support of the present invention is provided with an attachment which is identified as a whole with reference numeral 5. The attachment 5 has a base 6 which is attachable to the inner surface of the supporting element 1. The base 6 can be attached to the supporting element 1 by interengaging formations which are formed on the facing surfaces of the base 6 and a portion of the supporting element 1 and shaped as interengaging hooks and loops as well known in the art. The base carries a plurality of individual plates 7 each provided with a plurality of pressure producing projections and spaced from one another in mutually perpendicular directions. The plates 7 are connectable with the base 6 for example by rivets 9 so that they can slightly turn around the axis of the rivet. As can be seen from the drawings, each rivet 9 is located in a center of each plate 7, while the projections 8 are located substantially around the rivet. While the base 6 can be composed for example of fabric, the plates 7 together with the projections 8 can be composed of plastic. The projections 8 project from an inner surface of the plate 7 and can narrow in direction away from the plate and also can be pointed at their free ends. The projections 8 of each plate are spaced from one another in mutually perpendicular directions. The base 6 can be also somewhat stretchable, as well as a portion of the supporting element 1 onto which the base 6 of the attachment 5 is attached.

In order to obtain a corresponding pain-alleviating and/or healing effect, the lumbo-sacral support is placed on a user, so that its inner surface faces the user's back area. When the supporting element 1 is closed, in addition to the supporting action by the supporting element 1 which tightly embraces the user's body, the projections 8 apply an acu pressure to a plurality of points on the user's body in a corresponding area.

It will be understood that each of the elements described above, or two or more together, may also find a useful application in other types of constructions differing from the types described above.

While the invention has been illustrated and described as embodied in lumbo-sacral support, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A lumbo-sacral support, comprising a support, comprising a supporting element placeable on a user's body and having an outer surface and an inner surface adapted to face a user's body, said supporting element having opposite ends connectable with one another and being provided on said inner surface with a plurality of projections to apply pressure to the user's body; an attachment element which is attended to said inner surface of said supporting element and is provided with a plurality of said projections, said attachment element including a base attached to said inner surface of said supporting element and a plurality of plates connected with said base, each of said plates being provided with a plurality of said projections, each of said plates being turnable; and means for turnably connecting each of said plates to said base.

2. A lumbo-sacral support as defined in claim 1, wherein said plates are spaced from one another in two mutually perpendicular directions.

3. A lumbo-sacral support as defined in claim 1, wherein said projections are spaced from one another in two mutually perpendicular directions.

4. A lumbo-sacral support as defined in claim 1, wherein said projections of each said plates are spaced from one another in two mutually perpendicular directions.

5. A lumbo-sacral support as defined in claim 1, wherein said supporting element has a stretchable portion so as to be adjustable to a user's body.

6. A lumbo-sacral support, comprising a support, comprising a supporting element placeable on a user's body and having an outer surface and an inner surface adapted to face a user's body, said supporting element having opposite ends connectable with one another and being provided on said inner surface with a plurality of projections to apply pressure to the user's body; a plurality of plates which are attached to said supporting element and each provided with a plurality of projections adapted to apply a pressing action to the user's body; and means for turnably connecting each of said plates with said supporting element, said means for connecting each of said plates to said supporting element being located in a center of each of said plates, while said projections are located substantially around said connecting means.

* * * * *